US006485984B1

United States Patent
Kim

(10) Patent No.: US 6,485,984 B1
(45) Date of Patent: Nov. 26, 2002

(54) CALIXCROWN DERIVATIVES, A PROCESS FOR THE PREPARATION THEREOF, A SELF-ASSEMBLED MONO-LAYER OF THE CALIXCROWN DERIVATIVES PREPARED BY USING THE SAME AND A PROCESS FOR IMMOBILIZING A PROTEIN MONO-LAYER BY USING THE SELF-ASSEMBLED MONO-LAYER OF THE CALIXCROWN DERIVATIVES

(75) Inventor: Tai-Sun Kim, Seoul (KR)

(73) Assignee: Proteogen, Inc. (KR)

( * ) Notice: Subject to any disclaimer, the term of this patent is extended or adjusted under 35 U.S.C. 154(b) by 12 days.

(21) Appl. No.: 09/632,157

(22) Filed: Aug. 3, 2000

(51) Int. Cl.$^7$ .................... G01N 33/553; G01N 33/545; G01N 33/552; C07D 323/00

(52) U.S. Cl. ................... 436/525; 435/7.4; 436/527; 436/531; 436/532; 530/391.1; 549/348

(58) Field of Search ................ 549/348; 436/525, 436/527, 531, 532; 530/391.1; 435/7.4

(56) References Cited

U.S. PATENT DOCUMENTS

| | | | | |
|---|---|---|---|---|
| 4,556,700 A | * | 12/1985 | Harris et al. | |
| 4,695,615 A | * | 9/1987 | Leonard et al. | |
| 5,143,784 A | * | 9/1992 | Mita | |
| 5,412,114 A | * | 5/1995 | Shinkai et al. | |
| 5,607,591 A | * | 3/1997 | Dozol et al. | |
| 6,117,413 A | * | 9/2000 | Fisher et al. | |

OTHER PUBLICATIONS

Arduini et al., "Synthesis of 1,2–Bridged Calix[4]arene–bi-scrowns in the 1,2–Alternate Conformation," *Tetrahedron*, 53:(10) 3767–3776. (1997).

Casnati et al., "Synthesis, Complexation, and Membrane Transport Studies of 1,3–Alternate Calix[4 ]arene–crown–6 Conformers: A New Class of Cesium Selective Ionophores," *J. Am. Chem. Soc.*, 117:(10) 2767–2777, (1995).

Müller et al., "Attempts to Mimic Docking Processes of the Immune System: Recognition–Induced Formation of Protein Multilayers," *Science*, 262: 1706–1708, (1993).

Huisman et al, Tetrahedron Letters, 36(18), 3273–3276 (1995).*

Andruini et al, Tetrahedron, 52(16), 6011–6018 (1996).*

* cited by examiner

*Primary Examiner*—Mary E. Ceperley
(74) *Attorney, Agent, or Firm*—Heller Ehrman White & McAuliffe LLP

(57) ABSTRACT

The present invention is to provide calixcrown derivatives of formulae 1 to 3 requisite for the preparation of a self-assembled monolayer as well as a process for the preparation thereof. Further the present invention is to provide a self-assembled monolayer which is produced by immersing a gold substrate or related metal substrate in an organic solution containing said calixcrown derivatives of formulae 1 to 3. Still further the present invention provides a process for fixing a protein monolayer by fixing proteins having molecular weight of not less than 20,000D (20KD) on said self-assembled monolayer.

8 Claims, 4 Drawing Sheets

[Fig. 1]
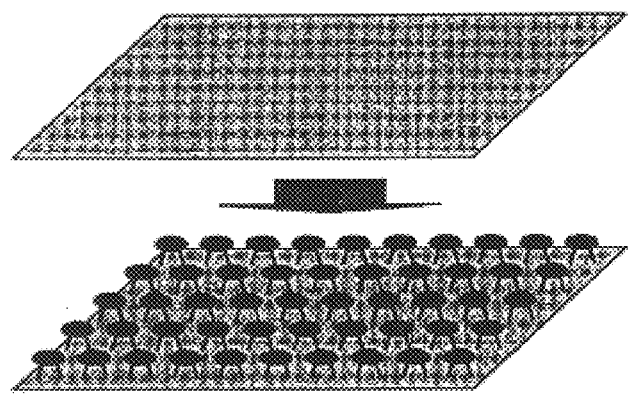
Calixcrown self-assembled monolayer
 = Calixcrown
[Fig. 2]
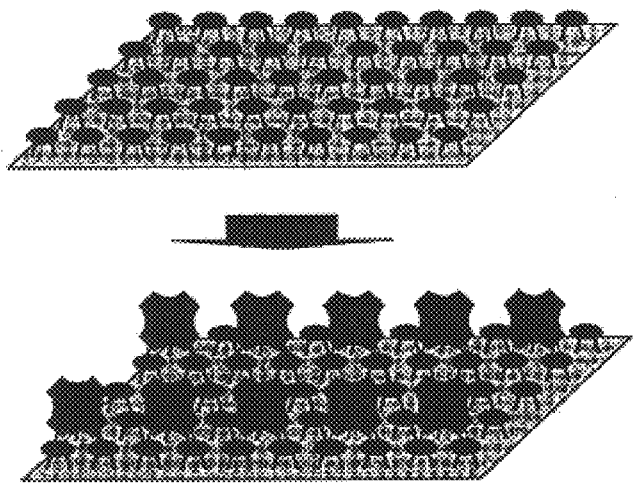
Protein monolayer
  Protein (antigen, antibody, enzyme)
$NH_3$

[Fig. 3]
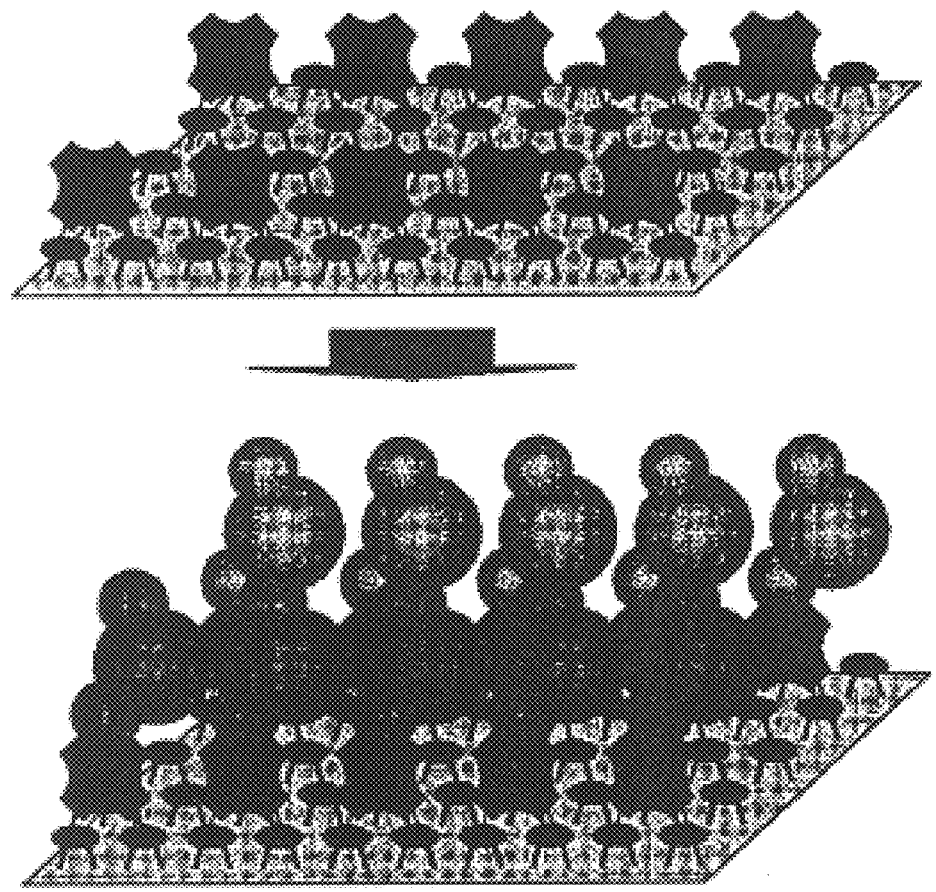
Protein double layer
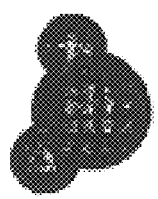 = Protein (antigen, antibody, enzyme)

[Fig. 4]
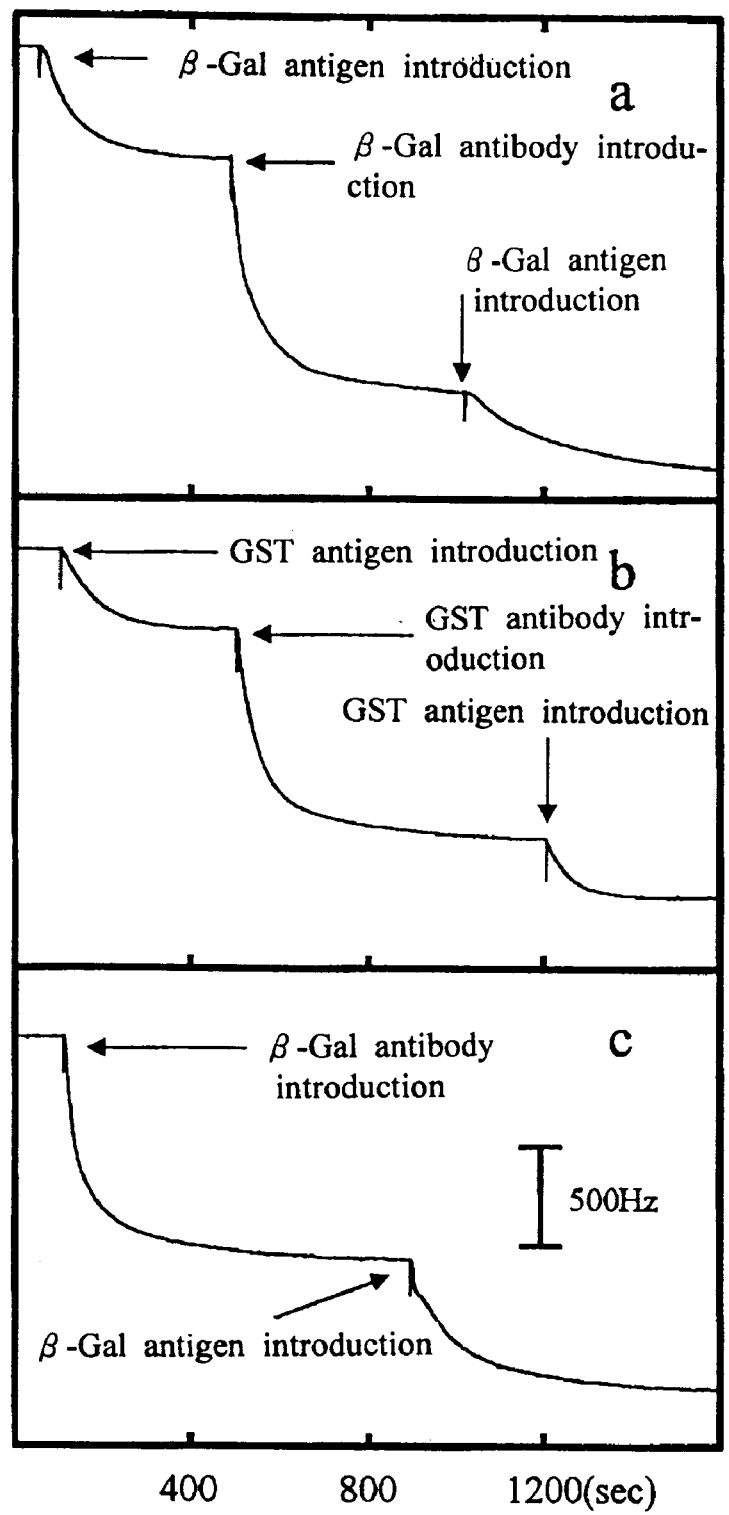

[Fig. 5]
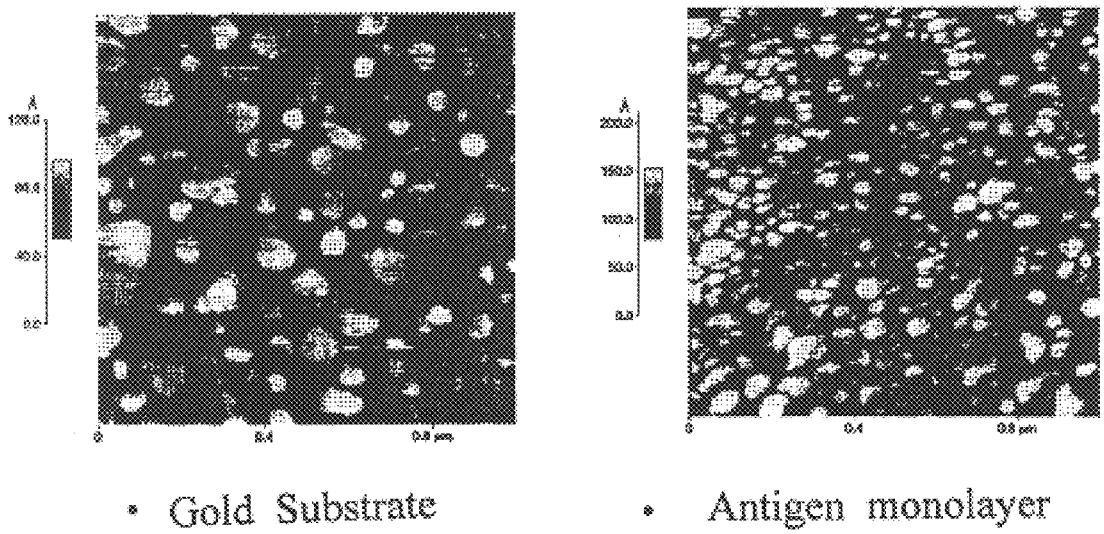
• Gold Substrate    • Antigen monolayer
[Fig. 6]
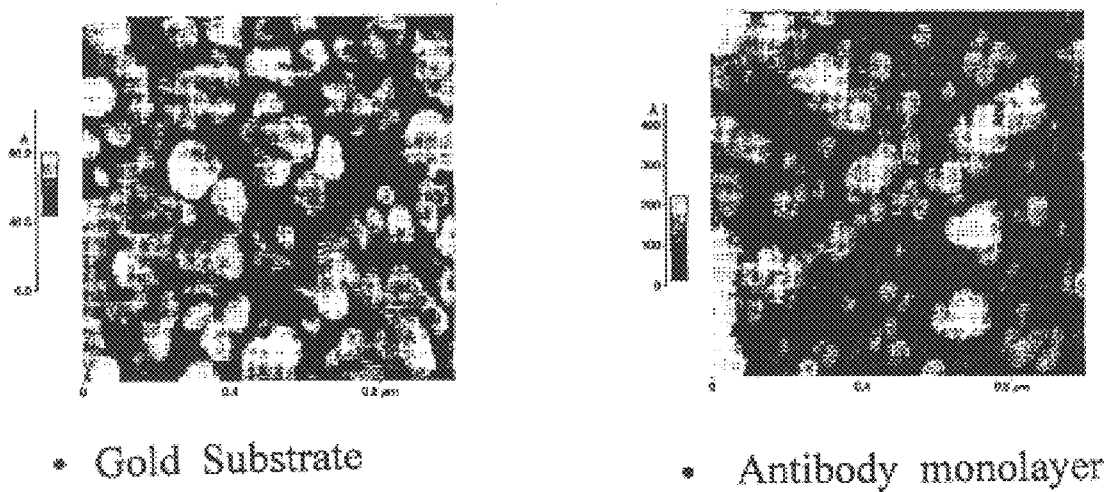
• Gold Substrate    • Antibody monolayer

CALIXCROWN DERIVATIVES, A PROCESS FOR THE PREPARATION THEREOF, A SELF-ASSEMBLED MONO-LAYER OF THE CALIXCROWN DERIVATIVES PREPARED BY USING THE SAME AND A PROCESS FOR IMMOBILIZING A PROTEIN MONO-LAYER BY USING THE SELF-ASSEMBLED MONO-LAYER OF THE CALIXCROWN DERIVATIVES

TECHNICAL FIELD

The present invention relates to novel calixcrown derivatives, a process for the preparation thereof, a self-assembled monolayer prepared by using the same and a process for immobilizing a protein monolayer by using the self-assembled monolayer of the novel calixcrown derivatives. In particular, the present invention relates to novel calixcrown derivatives having thiol functions indispensable for the preparation of a self-assembled monolayer of said calixcrown derivatives, which can be applied for immobilization of proteins by multiple ionic recognition. The present invention further relates to a process for the preparation of said novel calixcrown derivatives, a self-assembled monolayer prepared by applying said calixcrown derivatives to a gold substrate or related metal substrate and a process for immobilizing a protein monolayer by using the self-assembled monolayer.

BACKGROUND

The immobilization of enzymes, antigens, antibodies and the like on solid carriers has become one of the most basic techniques in biotechnology or in protein research, such as immunochemistry and enzyme chemistry. For example, the enzyme linked immunosorbentassay (ELISA) is a technique that has been widely used in biotechnology for the assay of a particular protein or specific proteins causing a certain disease in experimental or clinical laboratories. Assay kits of such ELISA are commercially available in the market. More recently, development of protein chips, which require improved methods of protein immobilization on a solid matrix, is of a great concern in the field of biotechnology for the further advancement of proteomics research in the post-genomic era.

Previously, the immobilization of proteins such as antigens, antibodies or enzymes has been commonly practiced by physical adsorption of said proteins on a high molecular weight biopolymers such as various derivatives of collagen, dextran or cellulose. Covalent bonding between proteins and carrier surface by chemical reaction has been also widely used as a method for protein immobilization. The protein immobilization method by a "Sandwich" technique (triple-molecular layer) has been disclosed in literature [Science, 1993, Vol. 262, pp1706–1708], which describes a chemical bonding method by the biotin-avidin (or streptoavidin) interaction between proteins and carrier surface. That is, biotin is attached to the carrier surface and subsequently avidin or steptoavidin is linked thereto. Finally, proteins linked with biotin can be immobilized on said chemically modified carrier surface.

However, numerous problems are present in the various methods of protein immobilization described above. The physical adsorption method as well as the methods of covalent bonding and the biotin-avidine binding, which have recently been used, do bear problems as follows.

1. Density

The most critical problem of the protein immobilization method used in the past has been noted as that the amount of protein immobilized on the surface of a substrate is extremely small. When the density of a protein to be immobilized on a carrier surface is low, other proteins may form non-specific binding. It is thus necessary to carry out chemical treatment for the carrier surface so as to eliminate the undesired proteins bound to the carrier surface. However, such a chemical treatment may cause inactivation or denaturation of the immobilized protein molecule. In addition, even if a specific target protein is immobilized successfully onto the surface of a carrier, only an extremely small amount of the protein can be captured and consequently, it is often required that the assay result be further confirmed by various assay methods. It is also noted that the more the amount of proteins is immobilized on an unit area on the surface of a carrier, the easier the assay process is. In this regard, many studies have been carried for the development of methods for a single molecular layer of proteins with the maximum amount immobilized on a carrier surface. A satisfactory result, however, is yet to be achieved.

2. Activity

In prior methods for protein immobilization by either chemical bonding or physical adsorption on surface of a carrier, the activity of an immobilized protein could be decreased in comparison with the free protein in a solution. It has been known as the reason that an immobilized protein on a solid carrier could lose its activity due to conformational changes or denaturation of the protein especially around its active site as it binds tightly to the carrier surface via physisorption or chemical binding.

3. Orientation

In prior methods for protein immobilization on surface of a carrier, an active site of the protein may become essentially oriented toward the carrier surface in such a way that the active site is masked and thus the activity of the protein becomes lost. Such orientation of the protein is also a serious problem in procedures of protein immobilization. It is known that such phenomena is occurred in almost half of the immobilized proteins.

OBJECT OF THE INVENTION

An object of the present invention is to provide calixcrown derivatives having two recognition sites essential as a molecular linker applicable for protein immobilization onto the surface of a carrier, one of which can recognize the ammonium residue of a protein while the other can bind tightly to the surface of a carrier; said calixcrown derivatives are active for the formation of a self-assembled monolayer, which is useful for a- process of protein immobilization solving the problems of prior processes. Another object of the present invention is to provide a process for the preparation of said novel calixcrown derivatives.

A further object of the present invention is to provide a self-assembled monolayer of calixcrown derivatives by binding said calixcrown derivatives on a gold substrate or related metal substrate; said monolayer of calixcrown derivatives can be used for high-density protein immobilization on a monolayer, the surface of which can allow to interact with all kinds of other proteins in a test solution thereof without any additional complicated procedures.

A further object of the present invention is to provide a immobilization process for protein molecules such as antigens, antibodies or enzymes of which the molecular weight are respectively not less than 20,000 D (20KD) on said self-assembled monolayer.

A further object of the present invention is to provide an immobilization process for said protein molecules by applying the compounds of formulae 1 to 3 of the present invention onto inorganic or organic solid substrate such as gold, silver, glass, silicon, polystyrene, polycarbonate, etc. for the preparation of protein chip, diagnostic kit, protein separation pack, etc.

BRIEF DESCRIPTION OF DRAWINGS

FIG. 1 is a schematic diagram showing the process for producing the self-assembled monolayer of calixcrown derivatives in the present invention.

FIG. 2 is a schematic diagram showing the immobilization process for the monolayer of proteins in the present invention.

FIG. 3 is a schematic diagram representing the recognition processes between the proteins in a solution and a monolayer of antigens or antibodies to study the activity of the protein monolayer prepared in FIG. 2.

FIG. 4 is a diagram of time courses of the formation of a protein monolayer, where the protein is either antibody or antigen and kinetic results of antigen-antibody interaction after introducing a binding protein with respect to said protein monolayer.

FIG. 5 is a photograph of an atomic force micrograph showing the monolayer of β-galactosidase antigen bound onto the calixcrown monolayer self-assembled on the gold substrate.

FIG. 6 is a photograph of an atomic force micrograph showing the monolayer of β-galactosidase antibody bound onto the calixcrown monolayer self-assembled on the gold substrate.

DISCLOSURE OF THE INVENTION

The present invention relates to novel calixcrown derivatives of formulae 1 to 3, which are indispensible for the formation of a self-assembled monolayer useful in the process of protein immobilization.

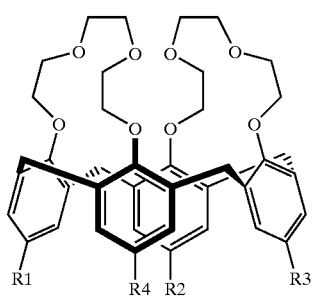

[Formula 1]

wherein R1, R2, R3 and R4 independently represent —$CH_2SH$, or a pair of the each side chains can form —$CH_2$—S—S—$CH_2$—, respectively; or R1, R2, R3 and R4 independently represent —$CH_2Cl$, —$CH_2CN$, —$CH_2CHO$, —$CH_2NH_2$, or —$CH_2COOH$.

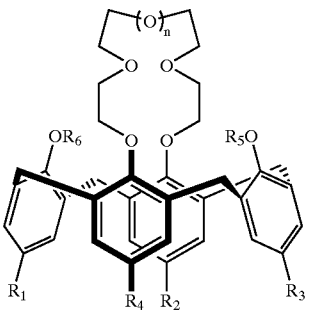

[Formula 2]

wherein n is 1; R1, R2, R3 and R4 independently represent —$CH_2SH$, —$CH_2Cl$, —$CH_2CN$, —$CH_2CHO$, —$CH_2NH_2$, or —$CH_2COOH$; or R1 and R3 represent —$CH_2SH$, —$CH_2Cl$, —$CH_2CN$, —$CH_2CHO$, —$CH_2NH_2$, or —$CH_2COOH$, and R2 and R4 represent H; and R5 and R6 represent H, methyl, ethyl, propyl, isopropyl or isobutyl, respectively.

[Formula 3]

wherein n is 2; R1, R2, R3 and R4 independently represent —$CH_2SH$, —$CH_2Cl$, —$CH_2CN$, —$CH_2CHO$, —$CH_2NH_2$, or —$CH_2COOH$; or R1 and R3 represent —$CH_2SH$, —$CH_2Cl$, —$CH_2CN$, —$CH_2CHO$, —$CH_2NH_2$, or —$CH_2COOH$, and R2 and R4 represent H; and R5 and R6 represent H, methyl, ethyl, propyl, isopropyl or isobutyl, respectively.

Said compounds of formulae 1 to 3 can generally be termed calixcrown derivatives, specifically the compound of formula 1 is termed calix[4]aren-biscrown-4, the compound of formula 2 is termed calix[4]aren-crown-5 and the compound of formula 3 is termed calix[4]aren-crown-6, respectively.

The starting material for the synthesis of the compounds of formulae 1 to 3 are compounds of calix[4]aren-biscrown-5 or -6 wherein R1, R2, R3 and R4 represent H, R5 and R6 represent —$CH_3$ and compounds of calix[4]aren-biscrown-4 wherein R1, R2, R3 and R4 represent H, respectively. These starting materials can be prepared by the process disclosed in the literature [J. Am. Chem. Soc., 1995, Vol. 117, pp 2767–2777; Tetrahedron, 1997, Vol. 53, pp 3767–3776].

The compounds of formulae 1 to 3 of the present invention can be prepared by chloromethylation of the starting materials produced by the well known method to transform two or four residues of R1 to R4 into —$CH_2Cl$ and then, optionally transforming each chloride (Cl) into thiol (—SH), cyano (—CN), aldehyde (—CHO), amide (—$NH_2$) or carboxylic acid (—COOH) group, or each two Cls into disulfide (—S—S—), respectively, by a conventional method.

In usual chloromethylation reactions, the crown group is easily disrupted by Lewis acid ($SnCl_4$ and the like), which is used for chloromethyl groups to react with the crown moeity. However, according to the process of the present invention, it is possible to achieve chloromethylation reaction without affecting the crown moiety and to produce calixcrown derivatives at high yield. In the present invention, $CH_3$—O—$CH_2Cl$ is used as the chloromethyl-transforming reagent and SnC4 is used as Lewis acid. For the preparation of the compounds of formulae 1 to 3 wherein R1, R2, R3 and R4 have thiol groups or a pair of the each side chains forms disulfide bond, in order to convert chloromethyl groups into thiol groups or disulfide bonds, direct conversion to thiol groups with NaSH or converting them into thiol groups by reacting first with thiourea and refluxing the mixture in a basic solution of NaOH and the like can be applied. The compounds of formulae 1 to 3 can be prepared by said methods with a good yield.

Additionally, the present invention is to provide a self-assembled monolayer of calixcrown derivatives by affixing said compounds of formulae 1 to 3 to a gold substrate or related metal substrates; said self-assembled monolayer can be used to form a protein monolayer where all kinds of proteins can be bound on the surface without any complex procedures. Related metal substrates are understood to encompass noble metals such as Ag, Pt, etc.

Further, the compounds of formulae 1 to 3 may be coated onto a solid substrate such as inorganic and organic solid substrate, for example metal, glass, silicon, polystyrene, polycarbonate, etc.

FIG. 1 is a schematic diagram showing the process for producing a self-assembled monolayer of calixcrown derivatives according to the present invention. The detailed process for preparing a self-assembled monolayer of calixcrown derivatives is as follows:

A solution of the compounds of formulae 1 to 3 in an organic solvent such as $CHCl_3$ in the concentration of 1–3 mM is prepared. A gold substrate is introduced into said solution for 1 to 24 hours, washed with acetone and water respectively, and dried. A self-assembled monolayer of calixcrown derivatives is completely formed as shown in FIG. 1. The gold substrate of the present invention can be prepared in numerous shapes and are generally prepared by a method where chrome(Cr) or titanium(Ti) is vapor deposited under reduced pressure on glass, fused quartz, silicon wafer or plastics in a thickness of 5 to 10 nm followed by the vapor deposition of gold in thickness of about 200 nm. Before use the gold substrate prepared is immersed directly in a Piranha solution (a mixed solution of hydrogen peroxide and concentrated sulfuric acid in the ratio of about 1:2–3) for about one minute and washed with water. The gold substrate may also be boiled in the basic solution or may be passed through ozone in prior to use. After the cleaning, it is preferable to use the gold substrate immediately. The formation of the self-assembled monolayer of calixcrown derivatives is confirmed by the surface reflect infrared spectroscopic analysis.

Further, the present invention is to provide a process for immobilizing proteins by multiple ionic recognition at the crown group of the calixcrown derivatives interacting with cationic groups such as ammonium residues distributed in a great deal at the opposite side of active sites of proteins.

The process for protein immobilization of the present invention will be useful for the development of all kinds of protein chips as well as assaying methods for test proteins. At present, no other reports with similar findings have been reported.

The process for protein immobilization of the present invention can easily immobilize proteins on the surface of a solid carrier by multiple ionic recognition process, i.e., cationic groups recognizing the functional binding site of the crown group without any chemical treatment of protein molecules nor molecular transformation by genetic engineering, which has been employed in the previous conventional immobilization methods of proteins. Accordingly, the present invention provides an advanced method for the preparation of a densely populated protein monolayer on which a desired secondary protein can interact.

Said monolayer of a protein thus prepared has no problem of low concentration of bound proteins nor a problem of vacant sites remained for non-specific protein binding which is often seen in conventional methods of protein immobilization, and thus demonstrates no adverse affect caused for subsequent applications.

Since the present invention is based on the immobilization process by multiple ionic interaction of cationic groups in a protein molecule, the binding affinity of a protein to another is not too strong as seen in chemical bonding. Thus, the immobilization method of the present invention is clearly different from previously known methods of protein immobilization. As demonstrated by the formation of a double layer of protein molecules, the activity of bound proteins after the immobilization process remained intact indicating that the present invention provides a much better way of protein immobilization as compared with prior chemical methods, which may cause a substantial loss of protein activity due to a strong bond formation between target proteins and the carrier surface.

The problem of orientation can be solved adequately because the most dense portion of ammonium residues in most proteins such as antigens, antibodies and enzymes is usually located at the opposit side of active sites of a protein.

As seen in FIG. 3, a kinetic study of antigen-antibody reactions is carried out with a monolayer of antigen or antibody by determining time-dependent weight changes and demonstrated that all the immobilized antigen molecules are bound to the antibody molecules, or vice. The results confirmed that the process of the present invention provides a better method than prior methods in retaining activity of an immobilized protein on the monolayer of a protein prepared on a carrier surface.

FIG. 2 is a schematic diagram showing the immobilization of proteins such as antigens, antibodies and enzymes by multiple ionic recognition, wherein —$NH_3^+$ of proteins is spontaneously bound on the self-assembled monolayer prepared with the compounds of formulae 1 to 3 by the molecular recognition function of calixcrown molecules. When the self-assembled monolayer of the compounds of formulae 1 to 3 is immersed in a protein solution, the monolayer of protein molecules which cover completely the surface of the self-assembled monolayer is formed through by the spontaneous binding reaction at the recognition sites within 3 minutes to 1 hour. It was confirmed by surface analysis by a atomic force microscope and by use of a quartz crystal microbalance (QCM) that protein molecules are immobilized on the self-assembled monolayer of the compounds of formulae 1 to 3 forming a complete protein monolayer. The capacitance can also be determined by the use of cyclic voltammetry for an additional proof of the protein binding. In all cases, it is shown that the formation of a protein monolayer is completed in about one hour.

FIG. 3 represents the recognition process between the monolayer of antigen or antibody and proteins demonstrating activities of the protein monolayer prepared in FIG. 2.

The time-dependent changes in weight during the formation of either a monolayer or a double molecular layer of proteins are analyzed by the QCM method. As a result, it is observed that the degree of antibody interaction reached at a maximum level by the antigen-antibody interaction with the antigen monolayer; the degree of antigen binding is almost equivalent to that of antibody monolayer directly immobilized onto a carrier surface. Similarly, in the reaction of antigen in solution with a monolayer of antibody produced on a self-assembled monolayer of the compounds of formulae 1 to 3, the same result can be obtained as seen in the case of immobilizing an antigen monolayer directly on a self-assemble monolayer of the compounds of formulae 1 to 3. These results suggest that the activity of the protein bound to the self-assembled monolayer of the compounds of formulae 1 to 3 by multiple ionic interaction is remarkably good.

The process for preparing a monolayer of proteins in the present invention is as follows;

The self-assembled monolayer of calixcrown derivatives prepared as set forth herein above is immersed into a buffer solution containing proteins having molecular weight of not less than 20,000 D (20 KD) in a concentration of several nM to $\mu$M. After one hour to two hours, the monolayer is taken out to complete the formation of a protein monolayer. At this time, the lower the cation concentration in the buffer solution wherein protein is dissolved is, the faster the formation of the monolayer is. The process of monolayer formation was confirmed by determining weight change by the QCM measurement. The optimum concentration of cations for the formation of a protein monolayer is 0.083 mM to 1.4 mM phosphate buffer. The time required for the formation of a protein monolayer was determined to be longer than three hours as cation concentrations are too high or low, i.e., in the concentration more than 10 mM or less than 0.083 mM. Alternatively a buffer solution containing protein may be dropped or spotted onto the monolayer.

The density of protein molecules attached on the solid substrate after the formation of a protein monolayer can be directly confirmed by the observation with an atomic force microscope which can detect as accurately as a nanometer scale.

FIG. 5 and FIG. 6 are AFM images in a dimension of nanometer which show the monolayer formed by two kinds of proteins i.e., an antigen and antibody molecules arrayed on the self-assembled monolayer of calixcrown derivatives and the AFM images for the surface of gold substrate. It is noted that protein molecules are assembled on the entire gold surface forming a complete monolayer without leaving space for other protein molecules to bind.

On the other hand, viewing changes in thickness of a protein layer, it is presumed that should other proteins be bound on top of a protein monolayer, an increased thickness would have been detected in the dimension of several nanometers due to the molecular size of the protein applied. However such a difference has not been detected suggesting that the same kind of a protein does not bind on top of the protein monolayer by physical adsorption forming a double layer. Most of the proteins are assembled in a monolayer on the carrier surface. This result can be attributed to that the protein immobilization proceeds only with ammonium ions of a protein recognized by the crown ring, a moiety of molecular recognition function, of calixcrown derivatives of the present invention. Thus, if there is no more adequate space available within the protein monolayer prepared, no other protein may bind to the surface of gold substrate nor to the immobilized protein layer forming a multi-layer protein complex.

Said result is confirmed by weight changes determined by QCM. No weight change is observed even when the concentration of the same protein is increased after the formation of the monolayer is completed. It is suggested that the physical adsorption between the same kind of protein molecules does not occur once a protein monolayer is formed.

FIGS. 4a, 4b and 4c are graphical representations showing the formation of a protein monolayer by QCM which can detect weight changes of proteins bound on the surface at the level of nanogram to microgram.

When the weight of a protein bound on the surface is increased, the vibration number of the quartz plate is decreased accordingly. The decreased value of the vibration number is substituted into the following Saubery Equation to obtain a value of the weight change.

[Mathematic Formula 1]

$$\Delta f = -C_f \Delta m \qquad (1)$$

wherein the value of $C_f$ is $2.26 \times 10^2$ cm$^2$MHz/g, the change of 1 Hz indicates the weight change of 4.42 ng/cm$^2$. Based on the above formula, as shown in FIG. 4c, in the study with $\beta$-galactosidase ($\beta$-Gal) antibody having MW of 160 KD, the weight of the protein molecules immobilized on the surface is in a level of about 4.2 $\mu$g/cm$^2$, suggesting that about 26 picomoles of the molecule are bound on the surface. In the case of glutathion-S-transferase(GST) or $\beta$-galactosidase($\beta$-Gal) antigen with a relatively smaller molecular weight as shown in FIGS. 4a and 4b, it is noted that the weight of immobilized proteins on a carrier surface appears to be relatively small.

The fact that the immobilized proteins prepared according to the present invention retain relatively high activity can be acknowledged by determining the amount of antibody or antigen bound onto tie surface by the affinity of the antigen-antibody interaction. The interaction affinity can be determined by measuring of weight changes of the bound antigen or antibody corresponding to $\beta$-Gal applied, or by applying GST antibody in a concentration of 10 to 20% to the GST antigen monolayer.

FIG. 4b shows the weight change when GST antibody with a molecular weight of 150 KD is bound to the monolayer of GST antigen. It is demonstrated that a similar weight change occurs with $\beta$-Gal antibody (molecular weight: 160 KD), having a molecular weight similar to that of GST antibody, introduced in the respective antigen monolayer as shown in FIG. 4a.

FIG. 4c shows the weight change during a course of the formation of a monolayer of $\beta$-Gal antibody on a carrier surface, which is almost identical with that of $\beta$-Gal antibody being bound to the monolayer of $\beta$-Gal antigen forming a double protein layer as seen in FIG. 4a. This result indicates that when antibody molecules with a large molecular size are bound to a monolayer of antigens with a relatively smaller size, should the concentration ratio of antigen and antibody be 1:1, a layer of antibody thus formed is almost the same as the case of a monolayer of antibody formed by itself.

FIG. 4c shows that though an 1:1 antibody-antigen complex is formed, when an antigen with relatively small size is bound to an antibody monolayer, the weight change shows less than that of the antigen monolayer prepared because the total amount of the antigen molecule bound to the antibody is smaller than that of the antigen monolayer. During the preparation process of an antigen monolayer using a buffer solution containing the antigen at a concentration required for the formation of a monolayer, the subsequent application of additional antigen in a higher concentration caused no significant weight change. This result suggests that, once a monolayer is formed, there is no more deposition of the same protein bound by physical adsorption.

The solution of an antigen or an antibody used in the experiments is removed throughly before introducing an additional solution of protein. The above experiments allowed to demonstrate that the antigen or antibody immobilized on a carrier surface maintains sufficient activities so as to interact selectively with the corresponding counter proteins, i.e., the antigen-antibody interaction.

BEST MODE FOR CARRYING OUT THE INVENTION

The present invention will be understood in detail with reference to the following examples. However, these examples are not to be construed to limit the scope of the invention.

EXAMPLE 1

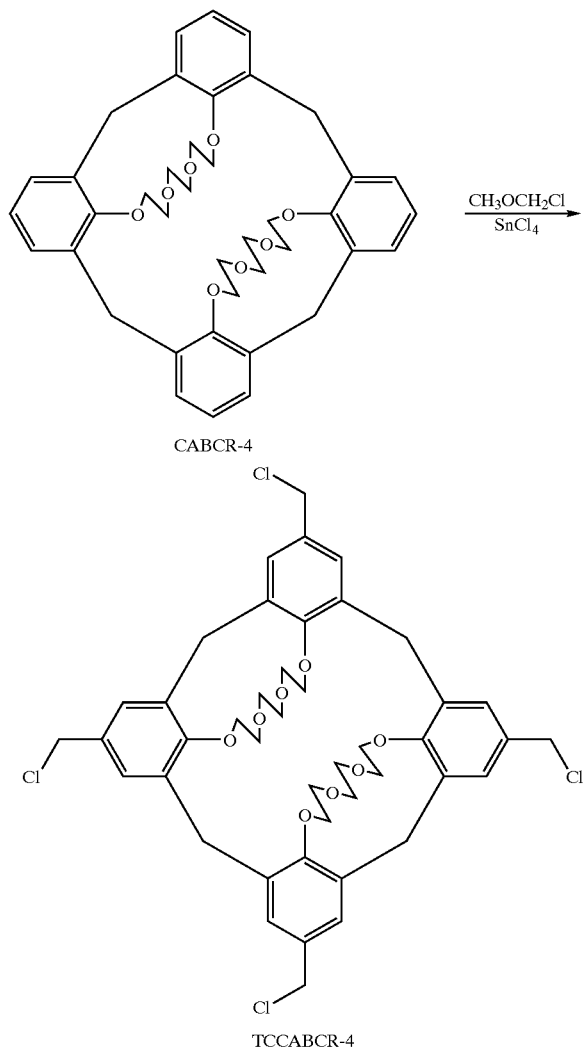

CABCR-4

TCCABCR-4

20 ml of CHCl$_3$ was introduced in a dry flask, which was then agitated under nitrogen atmosphere while being kept cold in an ice bath. Into the flask was added 0.468 ml (6.16 mmol) of CH$_3$OCH$_2$Cl and 2 minutes later 0.577 ml (4.93 mmol) of SnCl$_4$ was introduced in the flask gradually in 3 to 4 minutes. After 15 minutes, 100 mg (0.154 mmol) of calix[4]aren-biscrown-4 (CABCR-4) dissolved in an adequate amount (30 to 50 ml) of CHCl$_3$ was added gradually. 5 minutes later the ice bath was removed and the mixture solution was reacted for 1 hour while increasing the temperature to room temperature. In the reaction solution, an adequate amount (30 to 50 ml) of CH$_2$Cl$_2$ was added to dilute and excessive SnCl$_4$ was removed while agitating under cooling with ice. The organic layer was separated and washed twice with cold deionized water. The solution was dehydrated with a drying agent and the solvent was removed under reduced pressure to obtain the object compound of TCCABCR-4 (102 mg, 80% of the yield).

$^1$H NMR (400 MHz, CDCl$_3$): δ6.75–6.53 (8H, m), 4.98 (2H, d, J=13 Hz, ArCH$_2$Ar), 4.36–4.16 (18H, m, ArCH$_2$Ar, OCH$_2$CH$_2$O, CH$_2$Cl), 3.89–3.67 (16H m, OCH$_2$CH$_2$O), 3.22 (2H, d, J=13 Hz, ArCH$_2$Ar), and 3.12 (2H, d, J=13 Hz, ArCH$_2$Ar)

$^{13}$C NMR (400 MHz, CDCl$_3$): δ156.5, 135.6, 134.4, 128.8, 73.5, 70.9, 70.2(—OCH$_2$CH$_2$O—), 46.6(CH$_2$Cl), 31.1, 29.8(ArCH$_2$Ar)

EXAMPLE 2

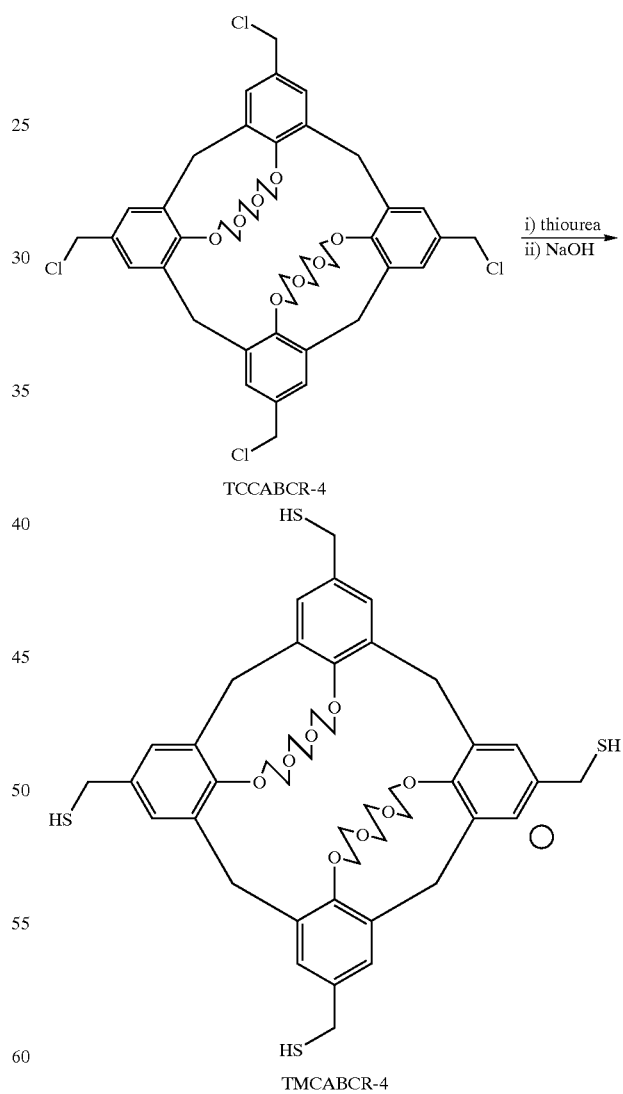

TCCABCR-4

TMCABCR-4

115 mg (0.136 mmol) of TCCABCR-4 and 41.3 mg (0.544 mmol) of thiourea were dissolved in 30 ml of ethanol. Ar gas was passed through the mixture solution for about 1 minute and the reaction was carried out under Ar gas atmosphere. The reactant was subjected to sonication at 45 to 55° C. for 60 minutes. 32.64 mg (0.816 mmol) of NaOH is added to the mixture to continue the sonication for 30 minutes. After the reaction was completed, pH was adjusted to 4 with 1N HCl. The reactant was dissolved in an adequate amount (30 to 50 ml) of $CH_2Cl_2$ and rinsed with water. The organic solvent was dehydrated and distilled off under reduced pressure. The resulted substance was purified by silica gel column chromatography (eluent: hexane-ethylacetate) to obtain 54 mg of TMCABCR-4. The process for changing —Cl to —SH using NaSH was carried out by sonication of the solution of NaSH for 8 times as much as TCCABCR-4 mole concentration in 30 ml of ethanol for 1 hour and being subjected to the same purification process. The resulted substance was obtained as the same yield as in the above reaction.

$^1$H NMR ($CDCl_3$): δ6.92–6.40 (8H, m, ArH), 4.91 (2H, d, J=13 Hz, $ArCH_2Ar$), 4.5–4.1 (8H, m, $OCH_2$), 4.29 (2H, d, J=13 Hz, $ArCH_2Ar$), 3.95–3.60 (20H, m, $OCH_2CH_2O$, $CH_2S$), 3.45 (4H, d, J=7.1 Hz, $CH_2S$), 3.19 (2H, d, J=13 Hz, $ArCH_2Ar$), 3.08 (2H, d, J=13 Hz, $ArCH_2Ar$), 1.54 (4H, t, J=7.1 Hz, SH)

$^{13}$C NMR ($CDCl_3$) : δ155.27, 135.49, 134.70, 134.42, 127.95, 127.84, 73.41, 70.91, 70.21, 31.15, 29.78, 28.68

EXAMPLE 3

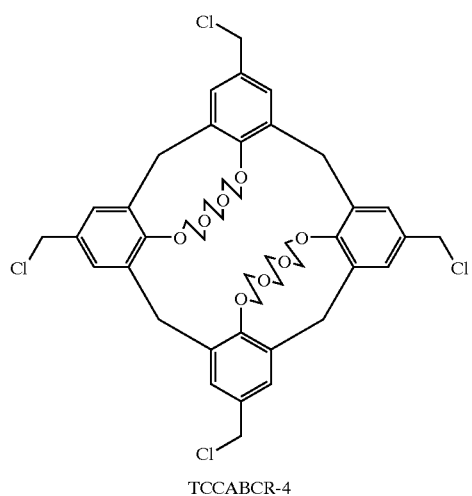

TCCABCR-4

1) thiourea
2) NaOH

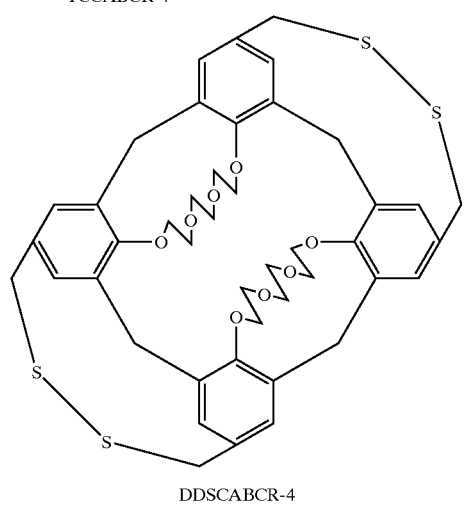

DDSCABCR-4

115 mg (0.136 mmol) of TCCABCR-4 and 41.3 mg (0.544 mmol) of thiourea were dissolved in 30 ml of ethanol. Without removal of oxygen in the solvent, the reaction was carried out. The reactant was subjected to sonication at 45 to 55° C. for 60 minutes. To the mixture 32.64 mg (0.816 mmol) of NaOH was added and the sonication was continued for 30 minutes. After the reaction was completed, pH was adjusted to 4 with 1N HCl. The reactant was dissolved in 30 to 50 ml of $CH_2Cl_2$ and rinsed with a water. The organic solvent was removed off under reduced pressure. The resulted substance was purified by silica gel column chromatography (eluent: hexane-ethylacetate) obtaining 60 mg of DDSCABCR-4.

$^1$H NMR ($CDCl_3$): δ6.81–6.50 (m, 8H, ArH), 4.92 (2H, d, J=13 Hz, $ArCH_2Ar$), 4.32–4.06 (m, 2H, $ArCH_2Ar$, 8H, —$OCH_2$—, 8H, —$CH_2S$—$SCH_2$—), 3.86–3.68 (m, 16H, —$OCH_2$—), 3.18–3.11 (4H, $ArCH_2Ar$)

$^{13}$C NMR ($CDCl_3$): δ155.7, 135.4, 134.5, 131.8, 128.1, 73.3, 72.6, 70.9, 70.4, 31.1, 29.7

EXAMPLE 4

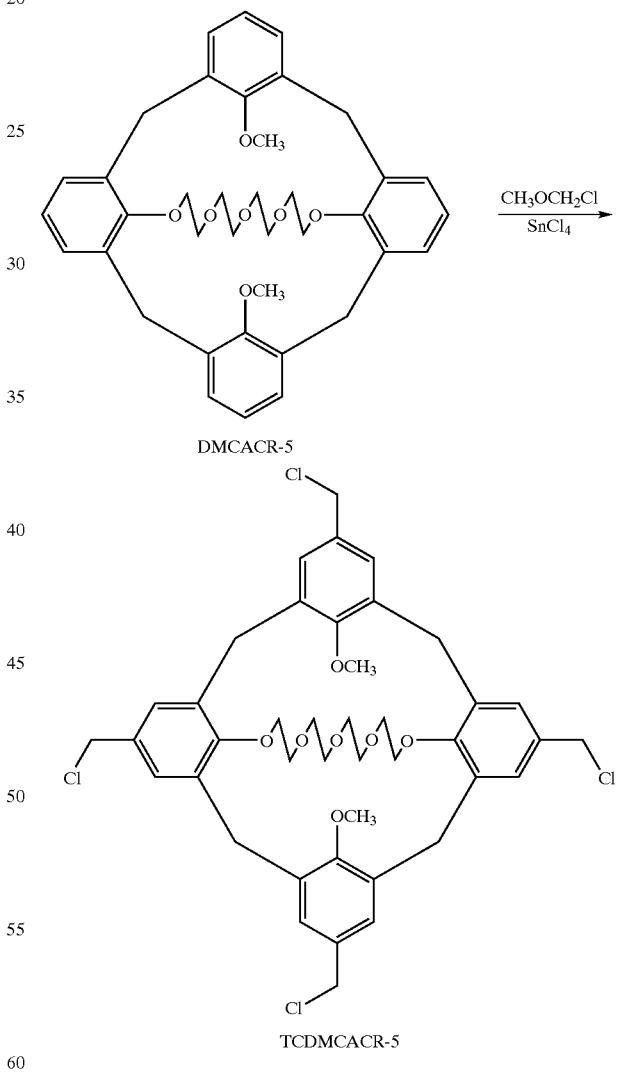

20 ml of $CHCl_3$ was introduced in a dry vessel, which was agitated under nitrogen atmosphere while being kept cold in an ice bath. To the vessel was introduced 0.515 ml (6.56 mmol) of $CH_3OCH_2Cl$ and about 2 minutes later, 0.612 ml (5.23 mmol) of $SnCl_4$ was added in 3–4 minutes. After 15 minutes, 100 mg (0.164 mmol) of 1,3-dimethoxycalix[4]

arencrown-5 (DMCACR-5) dissolved in an adequate amount (30 to 50 ml) of CHCl₃ was added to said reaction vessel gradually. After the addition of DMCACR-5 was completed, the solution was agitated in an ice-bath for 5 minutes and then the temperature of the solution was raised to room temperature in 10 minutes to be reacted for an hour. An adequate amount (30 to 50 ml) of CH₂Cl₂ was added to the reactant to be diluted and the excess SnCl₄ was removed while being agitated under the cool state added an ice. The organic layer was separated and washed with the cold deionized water twice. The solution was dehydrated with a drying agent and the solvent was distilled off under reduced pressure to obtain the object compound of TCDMCACR-4 (99 mg, 75% of the yield).

¹H NMR (CDCl₃): δ7.13 (4H, bs, ArH), 6.48 (4H, bs, ArH), 4.84–4.62 (8H, m, —CH₂Cl), 4.375 (4H, d, J=13 Hz, ArCH₂Ar), 4.14 (6H, s, —OCH₃), 3.99–3.58 (16H, m, —OCH₂—), 3.17 (4H, d, J=13 Hz, ArCH₂Ar),

¹³C NMR (CDCl₃): δ159.5, 155.7, 136.7, 133.8, 131.4, 128.9, 128.2, 126.9, 73.0, 71.5, 70.8, 70.6, 61.4, 46.9, 46.5, 31.1

EXAMPLE 5

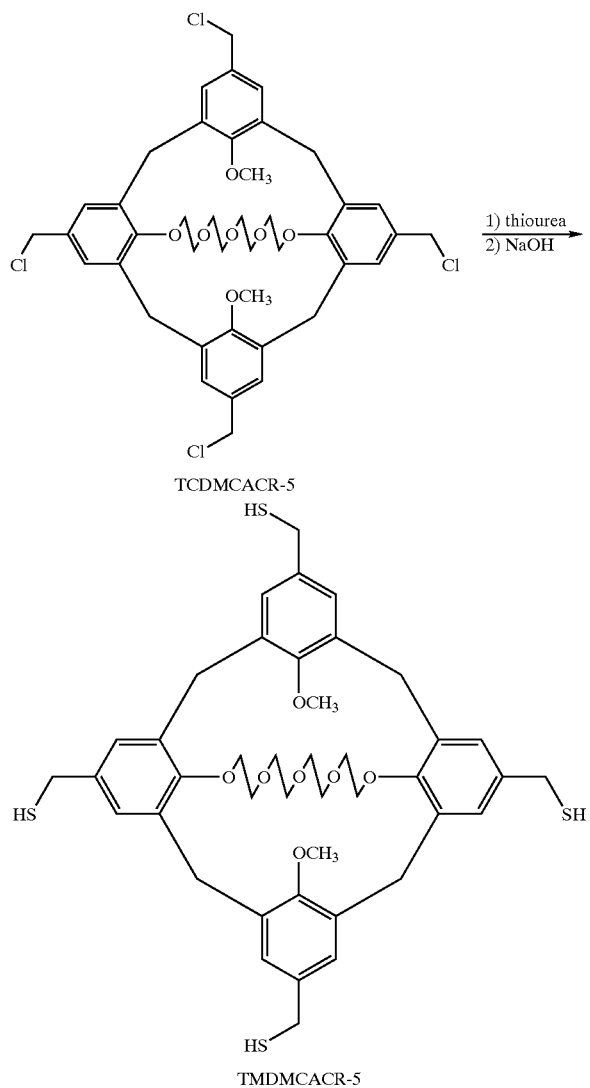

100 mg (0.124 mmol) of TCDMCACR-5 and 38 mg (0.50 mmol) of thiourea were dissolved in 25 ml of ethanol. Ar gas was passed through the mixture solution for about 1 minute and the reaction was carried out under Ar gas atmosphere. The reactant was subjected to sonication at 45 to 55° C. for 60 minutes. 30 mg (0.75 mmol) of NaOH was added to the mixture to continue the sonication for 30 minutes. After the reaction was completed, pH was adjusted to 4 with 1N HCl. The reactant was dissolved in an adequate amount (30 to 50 ml) of CH₂Cl₂ and rinsed with water three times followed by drying. The organic solvent was removed under reduced pressure. The resulted substance was purified by silica gel column chromatography (eluent: hexane-ethylacetate) obtaining 55 mg of TMDMCACR-5.

¹H NMR (CDCl₃): δ7.11–6.87 (4H, m, ArH), 6.52–6.45 (4H, m, ArH), 4.40–4.36 (4H, m, ArCH₂Ar), 4.12 (6H, s, —OCH₃), 4.06–3.40 (24H, m, —OCH₂—, —CH₂SH), 3.20–3.16 (4H, m, ArCH₂Ar)

¹³C NMR (CDCl₃): δ159.3, 155.4, 136.7, 133.6, 128.4, 127.6, 127.3, 122.5, 73.0, 71.5, 71.1, 70.8, 61.2, 31.1, 28.9, 28.4

EXAMPLE 6

The self-assembled monolayer of calixcrown derivatives in FIG. 1 was prepared by using TMDMCACR-5. A vacuum deposited gold substrate was cleaned and dried under nitrogen atmosphere. The substrate was immersed in the solution of an adequate amount (30 to 50 ml) of CHCl₃ for about 3 hours wherein TMDMCACR-5 was dissolved in the concentration of 2 mM. The gold substrate was washed with acetone and dried before used for preparation of the TMDMCACR-5 self-assembled monolayer.

When the substrate was assayed by an external reflection infrared spectrophotometric analysis (FT-IR-ERS), strong absorption bands of the C—O stretching mode characteristic of the crown group at 1040 cm⁻¹ and the aromatic stretching mode characteristic of calixaren at 1480 cm⁻¹ were observed. Thus it was confirmed that a monolayer of calixcrown derivatives was formed successfully on the surface of the gold substrate.

EXAMPLE 7

The protein monolayer shown in FIG. 2 can be prepared as the following.

The monolayer of calixcrown derivatives on the gold substrate prepared in Example 6 was immersed in 0.83 mM PBS buffer solution (phosphate buffer solution, containing Na⁺ and K⁺) containing β-galactosidase antigen at a concentration of 0.1 μM. 1 hour later, the monolayer was washed with buffer solution to form a monolayer of β-galactosidase antigen. The experimental result is reported in FIG. 4a, which shows the assay data by using a quartz crystal microbalance. After completion of the protein monolayer prepared, about 2.4 μg of antigen was immobilized in an area of 1 cm² of the monolayer. It took about 3 minutes for immobilization in QCM experiment to occur. FIGS. 5 and 6 show pictures taken using an atomic force microscope to measure the surface change of gold substrate arrayed on a glass plate and the antigen monolayer immobilized on the surface of the gold substrate coated with said calixcrown derivatives.

As seen in FIGS. 5 and 6, it is clearly noted that the surface configurations are different before and after the formation of the protein monolayer demonstrating the protein immobilized on the surface of gold substrate. Although the formation of a protein monolayer is completed in about 3 minutes, it is necessarily to take about 1 hour for an immobilized protein to endure the frictional force caused by the atomic force microscope tip during the observations.

In FIGS. 4a, 4b and 4c, the concentration of the proteins introduced first is 0.1 µM.

FIGS. 4a, 4b, and 4c are diagrams showing weight changes occurred when antigen or antibody protein in the concentration of 0.1 µM is introduced to the protein monolayers prepared with either antibody or antigen, respectively. In this experiments, it is demonstrated that the weight change on the surface when β-Gal antibody with molecular weight of 160 KD is bound to the monolayer of β-Gal antigen is nearly doubled in comparison with that of the antigen monolayer. FIG. 4b shows the weight change by GST antibody with molecular weight of 150 KD bound to the monolayer of light GST antigen appears almost equivalent to that of β-Gal antibody bound to the monolayer of the corresponding antigen. It is noted that such weight changes are just the same as the weights of the respective antigen or antibody bound to the surface of gold substrate as a monolayer. The result therefore suggests that the activity of the protein immobilized on the surface is almost completely preserved.

SIGNIFICANCE OF THE INVENTION

The present invention provides a novel process for immobilizing proteins by a system called 'molecular recognition' to solve possibly the problems of the conventional protein immobilization methods by chemical bonding or physical adsorption which have been widely used in the past.

According to the method of the present invention, any kind of proteins having molecular weight of not less than 20,000 D (20 KD) can be immobilized on a surface of a solid substrate within 1 hour without losing their activity; said method is characterized in that the solid substrate on the surface of which a self-assembled monolayer prepared by calixcrown derivatives of formulae 1 to 3 has been formed is immersed in a solution containing a protein to be immobilized. According to the present invention, protein molecules are tightly bound onto the surface of the substrate so that there may be no remaining space for other proteins to be possibly bound. In this way, the problem with prior conventional immobilization methods where non-specific binding of other protein molecules may occur is solved and simultaneously the chemical treatment used necessarily for eliminating the non-specific binding of other proteins need not be used. Consequently, the method of the present invention is time saving and economical, the activity of the immobilized protein is preserved intact; thus the present method is remarkably improved in comparison with prior protein immobilization methods.

Further the protein monolayer required for the recognition of a specific protein can be directly prepared for the further use according to the present invention, which will give enormous impacts for saving time and cost for preparation of immobilized proteins. Accordingly, the present invention has broad applications toward the future development of protein chips, diagnostic kits, and biosensors. The present invention has also solved stability problem of the crown functional groups, which degrades easily when calixcrown derivatives are prepared by conventional methods. The desired calixcrown molecules of the present invention can thus be synthesized at high yield.

What is claimed is:
1. Calix[4]aren-biscrown-4 derivatives of formula 1:

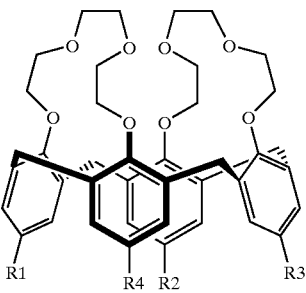

wherein R1, R2, R3 and R4 independently represent —CH$_2$SH, or a pair of side chains selected from R1 to R4 can form —CH$_2$—S—S—CH$_2$—, respectively; or R1, R2, R3 and R4 independently represent —CH$_2$Cl, —CH$_2$CN, —CH$_2$CHO, —CH$_2$NH$_2$, or —CH$_2$COOH.

2. Calix[4]aren-crown-5 derivatives of formula 2:

[Formula 2]

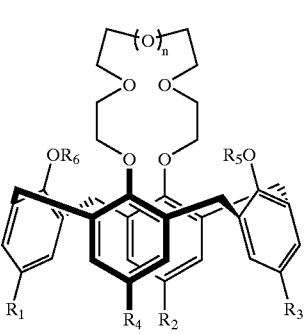

wherein n is 1; R1, R2, R3 and R4 independently represent —CH$_2$SH, —CH$_2$Cl, —CH$_2$CN, —CH$_2$CHO, —CH$_2$NH$_2$, or —CH$_2$COOH; or R1 and R3 represent —CH$_2$SH, —CH$_2$Cl, —CH$_2$CN, —CH$_2$CHO, —CH$_2$NH$_2$, or —CH$_2$COOH, and R2 and R4 represent H; and R5 and R6 represent H, methyl, ethyl, propyl, isopropyl or isobutyl, respectively.

3. Calix[4]aren-crown-6 derivatives of formula 3:

[Formula 3]

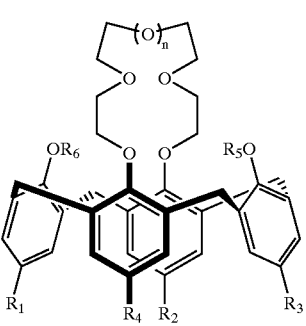

wherein n is 2; R1, R2, R3 and R4 independently represent —CH$_2$SH, —CH$_2$Cl, —CH$_2$CN, —CH$_2$CHO, —CH$_2$NH$_2$, or —CH$_2$COOH; or R1 and R3 represent —CH$_2$SH, —CH$_2$Cl, —CH$_2$CN, —CH$_2$CHO, —CH$_2$NH$_2$, or —CH$_2$COOH, and R2 and R4 represent H; and R5 and R6 represent H, methyl, ethyl, propyl, isopropyl or isobutyl, respectively.

4. A process for immobilizing proteins for the preparation of a protein chip, diagnostic kit or protein separation pack, which process comprises the steps of:

a) preparing a monolayer of calixcrown derivatives by applying the compounds according to any one of claims 1 to 3 onto an inorganic or organic solid substrate selected from the group consisting of gold, silver, glass, silicon, polystyrene, and polycarbonate;

b) immersing the monolayer prepared into a buffer solution in which a protein is dissolved.

5. A self-assembled monolayer of calixcrown derivatives according to any one of claims 1 to 3, characterized in that it is prepared by immersing a vacuum deposited gold substrate or related metal substrates for 1 to 24 hours in an organic solution in which the compounds according to any one of claims 1 to 3 are dissolved at a concentration of 1 to 3 mM.

6. A process for immobilization of proteins in a monolayer, characterized in that the self-assembled monolayer of calixcrown derivatives of claim 5 is immersed for 1 to 2 hours in a buffer solution in which a protein having a molecular weight of not less than 20,000 dalton is dissolved at a concentration of several micromole($\mu$M) to several nanomole(nM) to immobilize said proteins on said self-assembled monolayer.

7. A process for the preparation of calixcrown derivatives of formula 1 according to claim 1, which process comprises:

chloromethylating a compound of formula 1a:

[Formula 1a]

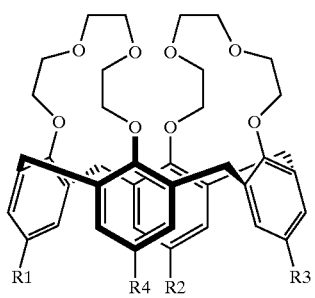

wherein

R1, R2, R3 and R4 are H to form a compound of Formula 1, wherein the side-chains of R1 to R4 are converted to —CH$_2$Cl; and then optionally each said Cl is converted to —SH, —CN, —CHO, —NH$_2$ or —COOH, or a pair of Cl's are converted to a disulfide bond (—S—S—).

8. A process for the preparation of calixcrown derivatives of formulae 2 or 3 according to claim 2 or 3, which process comprises:

chloromethylating a compound of formula 2b:

[Formula 2b]

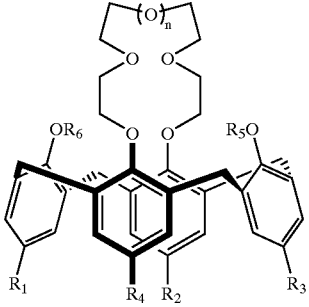

wherein n is 1 or 2;

R1, R2, R3 and R4 are H; and

R5 and R6 are —CH$_3$ to form a compound of Formula 2 or 3, wherein side chains R2 and R4 are H and side chains R1 and R3 are —CH$_2$Cl or side chains R1–R4 are —CH$_2$Cl;

then optionally each said Cl is converted to —SH, —CN, —CHO, —NH$_2$ or —COOH, or a pair of Cl's are converted to a disulfide bond (—S—S—).

* * * * *